US012101283B2

(12) United States Patent
Tomihisa

(10) Patent No.: US 12,101,283 B2
(45) Date of Patent: Sep. 24, 2024

(54) INFORMATION PROCESSING SYSTEM, CONTROL METHOD THEREOF, AND NON-TRANSITORY COMPUTER-READABLE STORAGE MEDIUM

(71) Applicant: CANON KABUSHIKI KAISHA, Tokyo (JP)

(72) Inventor: Taishi Tomihisa, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 208 days.

(21) Appl. No.: 17/841,764

(22) Filed: Jun. 16, 2022

(65) Prior Publication Data
US 2022/0407827 A1  Dec. 22, 2022

(30) Foreign Application Priority Data
Jun. 17, 2021 (JP) ................................. 2021-101026

(51) Int. Cl.
| | |
|---|---|
| H04L 51/07 | (2022.01) |
| A61B 5/00 | (2006.01) |
| A61B 5/16 | (2006.01) |
| G06V 20/00 | (2022.01) |
| G06V 40/10 | (2022.01) |
| G06V 40/20 | (2022.01) |
| G10L 25/63 | (2013.01) |

(52) U.S. Cl.
CPC .............. *H04L 51/07* (2022.05); *A61B 5/165* (2013.01); *G06V 20/35* (2022.01); *G06V 40/10* (2022.01); *G06V 40/20* (2022.01); *G10L 25/63* (2013.01); *A61B 5/0077* (2013.01); *A61B 5/4803* (2013.01)

(58) Field of Classification Search
None
See application file for complete search history.

(56) References Cited

U.S. PATENT DOCUMENTS

| | | | |
|---|---|---|---|
| 11,373,446 B1* | 6/2022 | Beisel | G10L 25/63 |
| 2016/0364002 A1* | 12/2016 | Gates | G06F 3/017 |
| 2019/0091403 A1* | 3/2019 | Osorio | A61M 5/1723 |
| 2019/0113973 A1* | 4/2019 | Coleman | G06F 3/011 |
| 2019/0228552 A1* | 7/2019 | Lee | G06T 11/60 |
| 2019/0266617 A1* | 8/2019 | Hwang | G06Q 50/01 |
| 2020/0148217 A1* | 5/2020 | Woo | B60W 40/09 |
| 2020/0162602 A1* | 5/2020 | Rakshit | H04M 1/72472 |
| 2021/0097142 A1* | 4/2021 | Breedvelt-Schouten | H04L 12/1822 |
| 2021/0110844 A1* | 4/2021 | Miyake | G06V 40/174 |
| 2021/0185276 A1* | 6/2021 | Peters | G06V 20/41 |
| 2022/0059122 A1* | 2/2022 | Xiu | G10L 17/04 |
| 2022/0086393 A1* | 3/2022 | Peters | G06V 20/41 |
| 2022/0407827 A1* | 12/2022 | Tomihisa | G10L 25/63 |

(Continued)

FOREIGN PATENT DOCUMENTS

WO    2018/174088 A    9/2018

*Primary Examiner* — Ricky Chin
(74) *Attorney, Agent, or Firm* — Venable LLP

(57) ABSTRACT

An information processing system is provided. The information processing system comprises: an analysis device configured to analyze emotion of a first person and quantify an emotion level of the first person; and an identification device configured to identify a second person serving as a communication target of the first person. The information processing system further comprises a notification device configured to notify the second person if the emotion level exceeds a set threshold.

14 Claims, 8 Drawing Sheets

(56) References Cited

U.S. PATENT DOCUMENTS

2023/0178217 A1\* 6/2023 Griffin ................... G16H 50/50
                                                              702/19
2023/0401976 A1\* 12/2023 Scanlon ................ G09B 5/065

\* cited by examiner

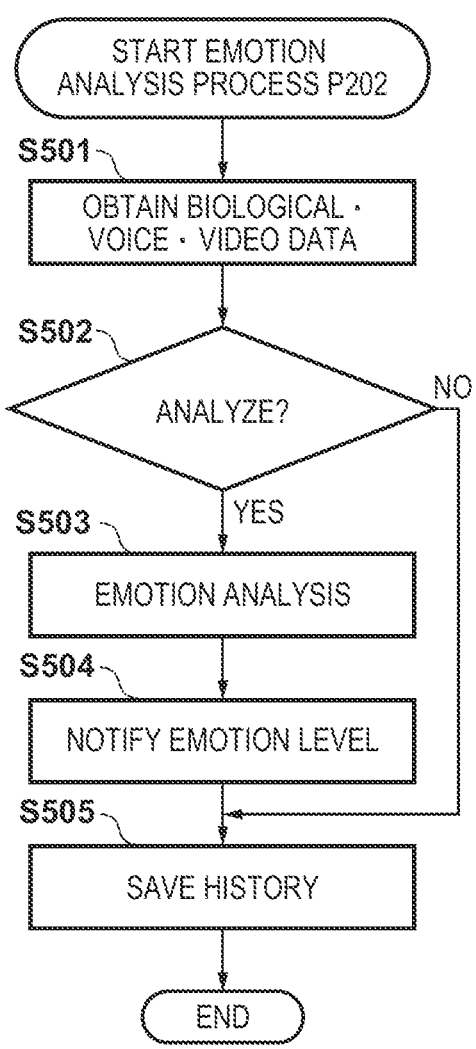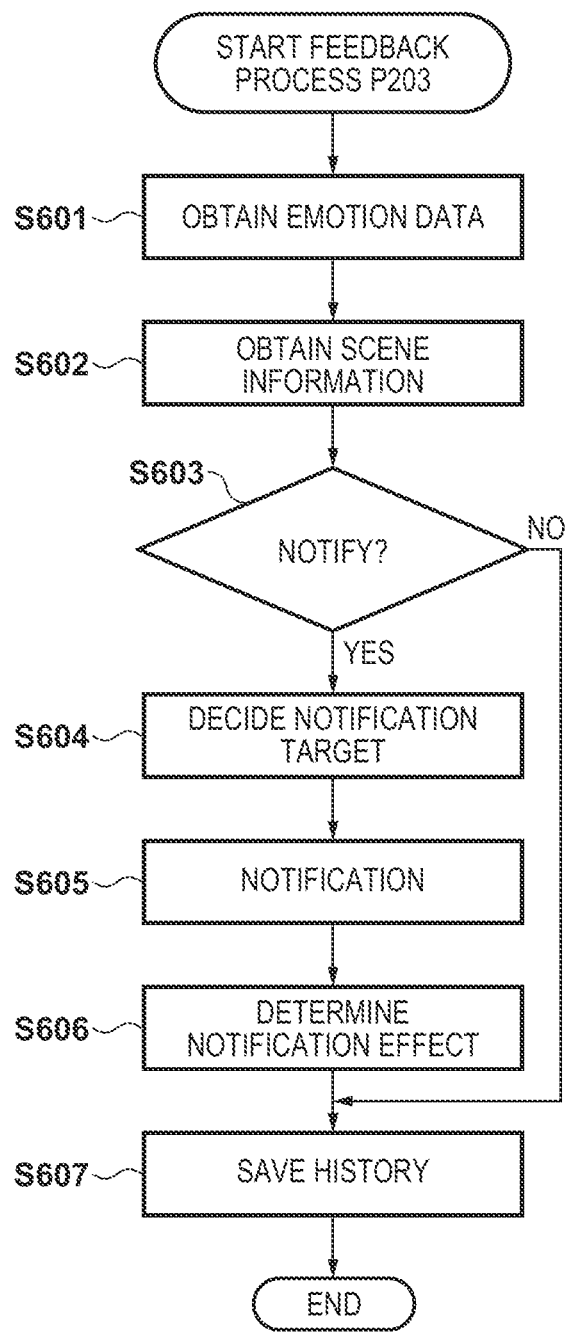

FIG. 7

| SCENE SPECIFICATION RESULT 700 | IMPORTANCE 701 | OUTPUT PRODUCT 702 | PERSON 703 | PLACE 704 |
|---|---|---|---|---|
| IMPORTANT REPORT | HIGH | RESULT REPORT | MATERIAL CREATOR, APPROVER, ... | EXECUTIVE CONFERENCE ROOM |
| IMPORTANT REPORT | HIGH | APPROVAL | MATERIAL CREATOR, AUTHORIZER, ... | APPROVER'S OWN DESK |
| CONSULTATION | LOW | TRAINING MATERIAL | GENERAL EMPLOYEE, MANAGER | GENERAL CONFERENCE ROOM |
| TEAM REVIEW | MEDIUM | SPECIFICATION | TEAM MEMBER, TEAM LEADER, ... | GENERAL CONFERENCE ROOM |
| INDIVIDUAL WORK | NONE | NONE | INDIVIDUALS (*NO COMMUNICATION TARGET) | INTERESTED PARTY'S OWN DESK |
| ... | ... | ... | ... | ... |

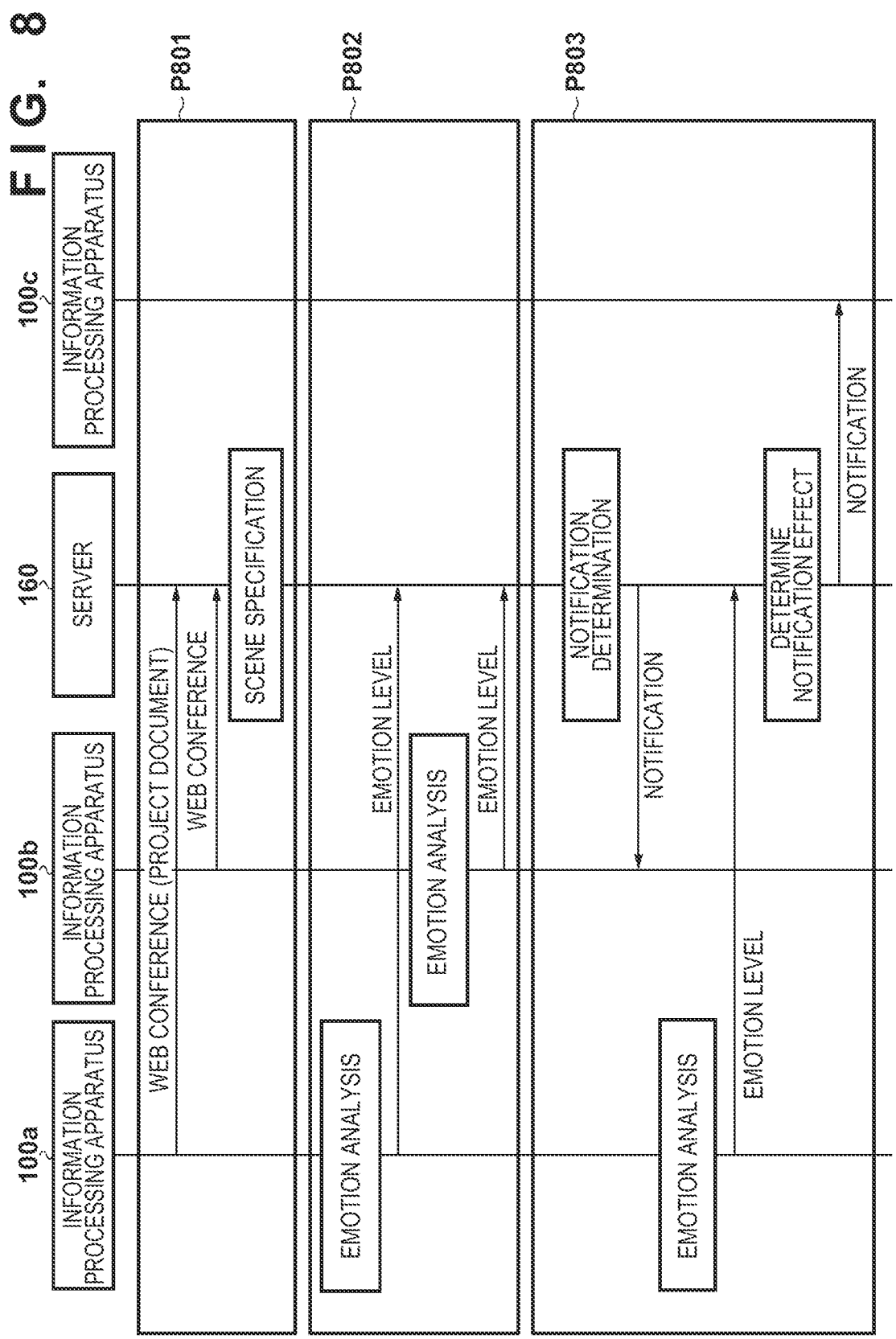

INFORMATION PROCESSING SYSTEM, CONTROL METHOD THEREOF, AND NON-TRANSITORY COMPUTER-READABLE STORAGE MEDIUM

BACKGROUND OF THE INVENTION

Field of the Invention

The present invention relates to an information processing system, a control method thereof, and a non-transitory computer-readable storage medium.

Description of the Related Art

With the diversification of people's values, it is sometimes difficult to smoothly communicate. International Publication No. 2018/174088 describes a communication analysis apparatus that evaluates the communication between a plurality of participants based on voice data and image data and provides the evaluation result to the plurality of participants in real time.

SUMMARY OF THE INVENTION

International Publication No. 2018/174088 describes analyzing the degree of participation of the participant in the communication, and encouraging the participant with a low degree of participation participate and speak. However, it may be difficult to enable participants having different values to communicate smoothly just by encouraging the participant with the low degree of participation to participate and speak.

Each of some embodiments of the present invention provides a technique advantageous in facilitating smooth communication.

According to some embodiments, an information processing system comprising: an analysis device configured to analyze emotion of a first person and quantify an emotion level of the first person; and an identification device configured to identify a second person serving as a communication target of the first person, wherein the system further comprises a notification device configured to notify the second person if the emotion level exceeds a set threshold, is provided.

According to some other embodiments, a control method of an information processing system, comprising: analyzing emotion of a first person and quantifying an emotion level of the first person; identifying a second person serving as a communication target of the first person; and notifying the second person if the emotion level exceeds a set threshold, is provided.

According to still other embodiments, a non-transitory computer-readable storage medium storing a program for causing a computer to execute a control method of an information processing system, comprising: analyzing emotion of a first person and quantifying an emotion level of the first person; identifying a second person serving as a communication target of the first person; and notifying the second person if the emotion level exceeds a set threshold, is provided.

Further features of the present invention will become apparent from the following description of exemplary embodiments (with reference to the attached drawings).

BRIEF DESCRIPTION OF THE DRAWINGS

FIG. 5 is a flowchart illustrating an example of a processing procedure of the information processing system shown in FIG. 1;

FIG. 6 is a flowchart illustrating an example of a processing procedure of the information processing system shown in FIG. 1;

FIG. 7 is a table showing examples of scenes of the information processing system shown in FIG. 1;

FIG. 8 is a view showing the sequence of processes of the information processing system shown in FIG. 1;

DESCRIPTION OF THE EMBODIMENTS

Figure 1:
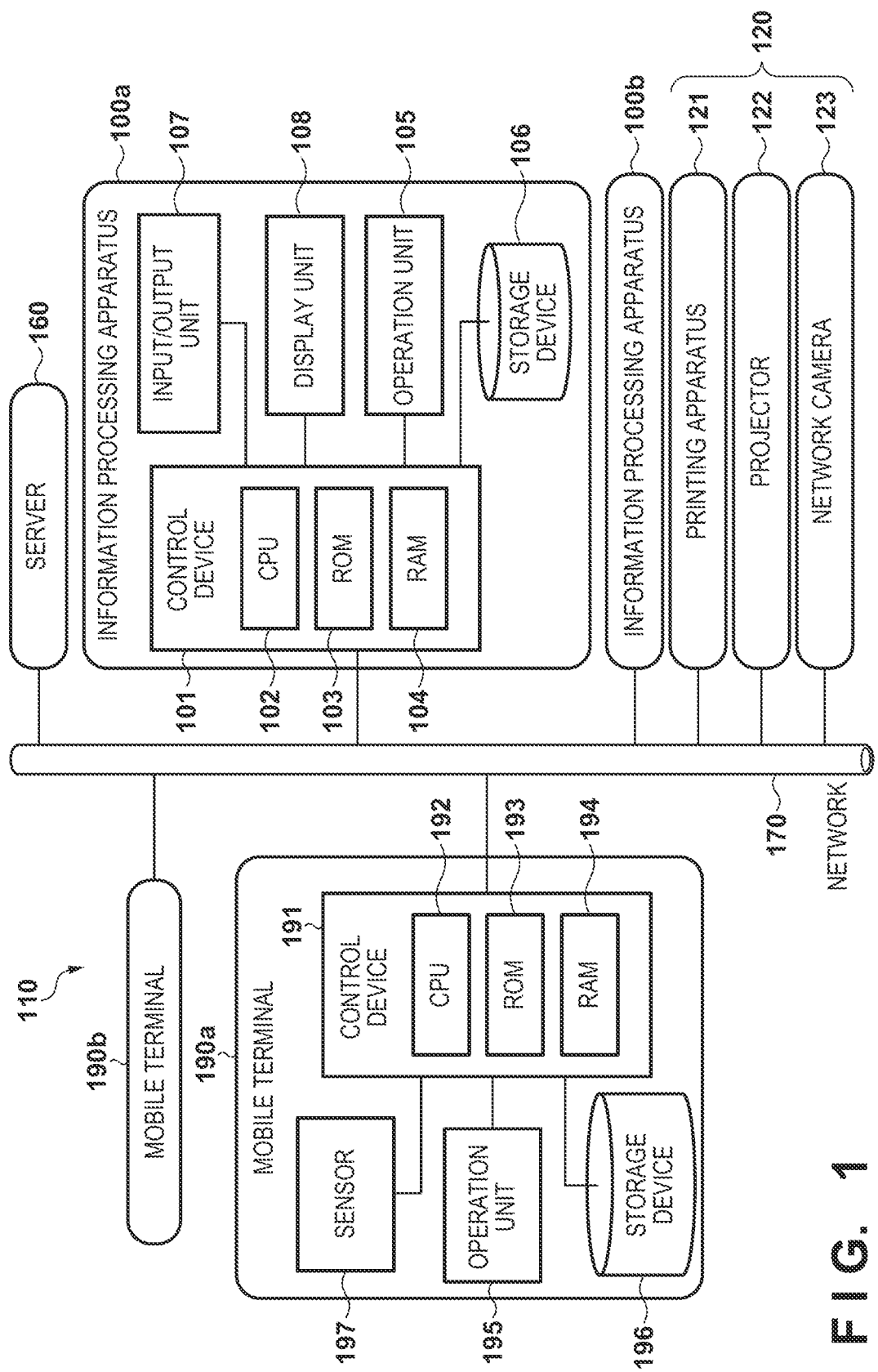
FIG. 1 is a block diagram showing a configuration example of an information processing system according to an embodiment.

Embodiments of the present invention will be described below in detail with reference to the accompanying drawings. Note that the following embodiments do not limit the claims of the present invention, and not all combinations of features set forth in the embodiments are essential to the present invention. Features set forth in the embodiments may be combined arbitrarily. The same reference numerals denote the same or similar parts and a repetitive description thereof will be omitted.

With reference to FIGS. 1 to 12, an information processing system according to an embodiment of the present invention will be described. FIG. 1 is a block diagram showing a configuration example of an information processing system 110 in this embodiment. As shown in FIG. 1, the information processing system 110 includes a mobile terminal 190, an information processing apparatus 100, and a server 160. As shown in FIG. 1, a plurality of the mobile terminals 190 may be arranged in one information processing system 110. Further, as shown in FIG. 1, a plurality of the information processing apparatuses 100 may be arranged in one information processing system 110. The server 160 may be, for example, a cloud server or the like. Similar to the mobile terminal 190 and the information processing apparatus 100, a plurality of the servers 160 may be distributed and arranged with respect to one information processing system 110. Here, in this specification, when indicating a specific one of the plurality of the mobile terminals 190 included in the information processing system 110, a suffix such as "a" or "b" is appended to a reference numeral like the "mobile terminal 190a". When it is unnecessary to distinguish between the mobile terminals, the mobile terminal will be simply referred to as the "mobile terminal 190". The same applies to the remaining components.

The mobile terminal 190, the information processing apparatus 100, and the server 160 are communicably connected to each other via a network 170 such as a LAN (Local Area Network) or a WAN (Wide Area Network). The network 170 may be a wired network or a wireless network. The network 170 may be formed by combining a wired network and a wireless network.

Further, another apparatus may be connected to the information processing system 110. In this embodiment, as shown in FIG. 1, peripheral apparatuses 120 including a printing apparatus 121, a projector 122, and a network camera 123 are connected to the information processing system 110.

The printing apparatus 121 can hold output data including the image information, the document information, and the like of an output product such as a printed product. The printing apparatus 121 may determine the contents of the output data based on the form type and description contents of the output product. The determination of the contents of the output data is not limited to be performed by the printing apparatus 121. The printing apparatus 121 may output the output data to the server 160, the information processing apparatus 100, or the mobile terminal 190, and the server 160, the information processing apparatus 100, or the mobile terminal 190 may determine the contents of the output data.

The projector 122 can hold display data including the projected image information, document information, and the like. The projector 122 may determine the contents of the display data based on the form type and description contents of the projected image or document. The determination of the contents of the display data is not limited to be performed by the projector 122. The projector 122 may output the display data to the server 160, the information processing apparatus 100, or the mobile terminal 190, and the server 160, the information processing apparatus 100, or the mobile terminal 190 may determine the contents of the display data. The projector 122 is merely an example of a display apparatus, and another apparatus such as a display that can display images and text may be used.

The network camera 123 can hold captured video data (video information and voice information) and behavior data that specifies a person, a place, and a behavior based on the video data. The behavior data is not limited to be specified by the network camera 123. The network camera may output the video data to the server 160, the information processing apparatus 100, or the mobile terminal 190, and the server 160, the information processing apparatus 100, or the mobile terminal 190 may specify the behavior data. The network camera 123 is merely an example of an image capturing apparatus, and another apparatus such as a still camera, a video camera, or a TV camera may be used.

The peripheral apparatuses 120 are not limited to the printing apparatus 121, the projector 122, and the network camera 123. By using the peripheral apparatuses 120, it is only required to obtain, based on the information of the image or document, for example, the information of the contents of a discussion and the information such as the behavior data indicating "when", "who", "where" and "what". For example, a meeting room use status management system that can grasp the entry/exit of the meeting room by using tools capable of specifying individuals such as employee ID cards may be used as the peripheral apparatus 120. Further, for example, a schedule management system that manages information such as "when", "who", and "discussion contents" may be used as the peripheral apparatus 120.

The mobile terminal 190 is formed by including an operation unit 195, a storage device 196, a sensor 197, and a control device 191. The control device 191 for controlling the respective components such as the operation unit 195, the storage device 196, and the sensor 197 in the mobile terminal 190 includes a CPU 192, a ROM 193, and a RAM 194. The CPU 192 comprehensively controls the respective components of the mobile terminal 190 based on an operating system program (to be sometimes referred to as an OS hereinafter) which is a control program stored in the ROM 193 or another storage medium. The RAM 194 is used as a work area of the CPU 192.

The operation unit 195 accepts an input from the user, displays an image, and the like. For example, the operation unit 195 may include a keyboard, a pointing device, and the like, or may include a touch panel display. The operation unit 195 informs the control device 191 of the information input by the user. The storage device 196 can be used as a work area of the CPU 192.

Further, the storage device 196 can store/save data. The sensor 197 is a component used to obtain the state of the user. For example, the sensor 197 can include a biological information sensor for obtaining biological information such as the heart rate, respiration rate, blood pressure, sweating, or body movement of the user. The sensor 197 can also include, for example, a microphone for obtaining voice information. The sensor 197 can also include, for example, a camera for obtaining video information. The sensor 197 may further include a loudspeaker for audio output. The sensor 197 outputs the data used to obtain the biological information, the voice information, the video information, and the like to the control device 191. The sensor 197 may analyze the biological information, the voice information, and the video information, or the control device 191 may analyze the biological information, the voice information, and the video information based on the data obtained by the sensor 197.

For example, the mobile terminal 190 may be in the form of a smart watch including an information processing function and a communication function. However, the present invention is not limited to this. For example, the mobile terminal 190 may include the sensor 197 for obtaining the biological information, and the voice information and the video information may be obtained by the information processing apparatus 100, the peripheral apparatus 120, or the like. As has been described above, the plurality of the mobile terminals 190 may be connected to one information processing system 110 via the network 170.

The information processing apparatus 100 includes a control device 101, an operation unit 105, a storage device 106, an input/output unit 107, and a display unit 108. The control device 101 is a control board (controller) that comprehensively controls the respective components in the information processing apparatus 100. The control device 101 includes a CPU 102, a ROM 103, and a RAM 104. The CPU 102 controls the respective components in the control device 101 via a system bus (not shown). For example, the CPU 102 executes a function of the information processing apparatus 100 by reading out and executing a program stored in the ROM 103, the RAM 104, the storage device 106, or another storage medium. The ROM 103 stores, for example, various kinds of control programs such as an operating system program (OS), and tables and setting data necessary for executing the function of the information processing apparatus 100. The RAM 104 is used as, for example, a work memory of the CPU 102. The storage device 106 stores, for example, various kinds of application programs, data, user information, device information, and the like.

The operation unit 105 may include a keyboard, a pointing device, and the like for accepting an input from the user, or may include a touch panel display. The operation unit 105 outputs the information such as the operation input by the user to the control device 101. The input/output unit 107 includes, for example, a microphone for audio input, a loudspeaker for audio output, a camera for image input, and the like, and outputs the obtained information to the control device 101. The display unit 108 is, for example, a liquid crystal display, and displays various kinds of user interface screens and information.

The arrangement of the server 160 may be similar to the arrangement of the information processing apparatus 100. Therefore, a detailed description will be omitted here.

Figure 2:
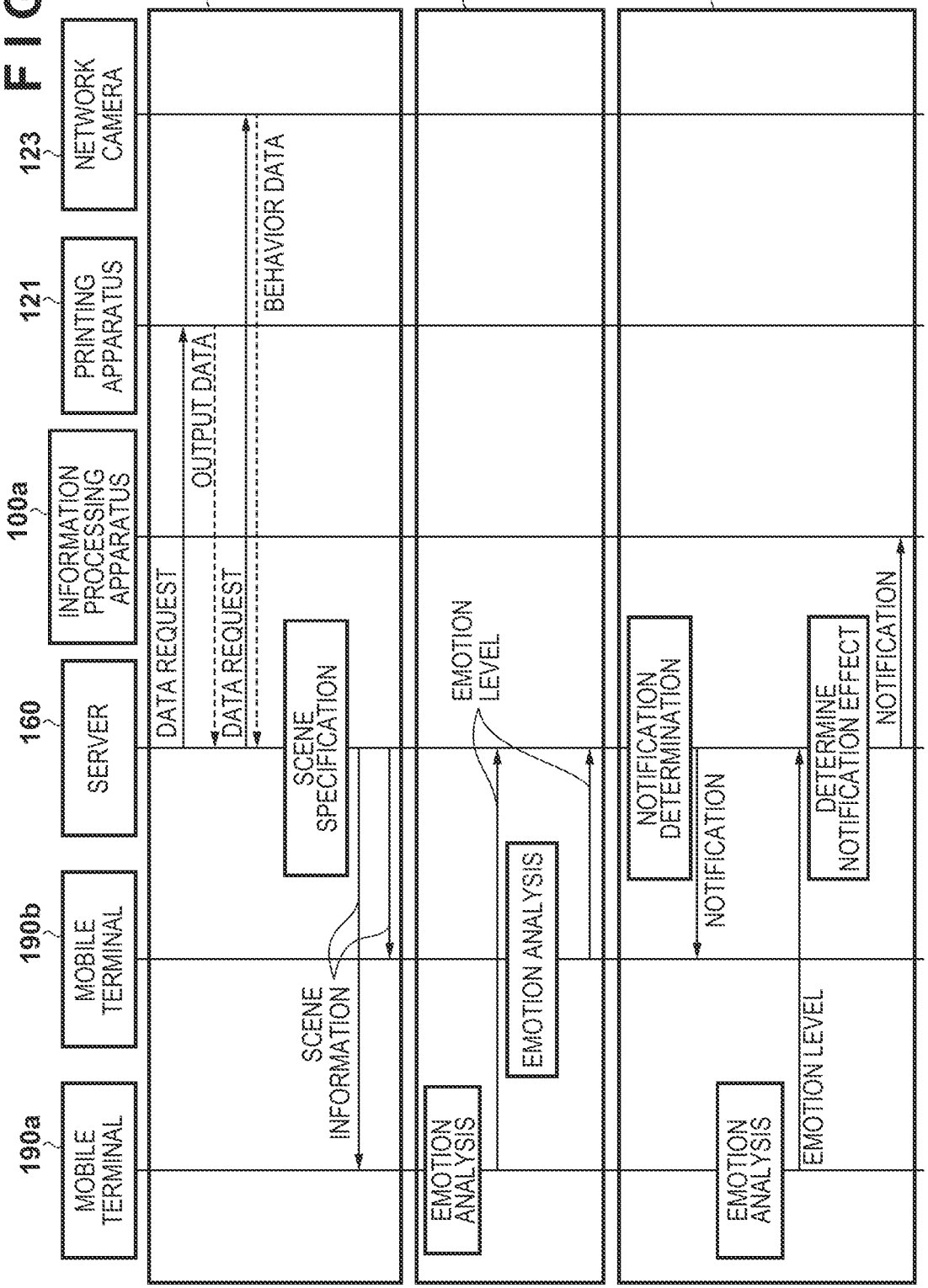
FIG. 2 is a view showing the sequence of processes of the information processing system shown in FIG. 1.

FIG. 2 is a view showing the procedure of processes of the information processing system 110 in this embodiment. The information processing system 110 executes three processes described below. The first process is a scene specification process P201 for specifying the scene of the communication space where participants communicate. The second process is an emotion analysis process P202 for analyzing the emotion of the person using the mobile terminal 190 and quantifying the emotion level of the person in the communication space. The third process is a notification process P203 for identifying a person serving as the communication target of the person whose emotion level is quantified, and notifying the person serving as the communication target if the emotion level exceeds a set threshold. The details will be described below.

Figure 3:
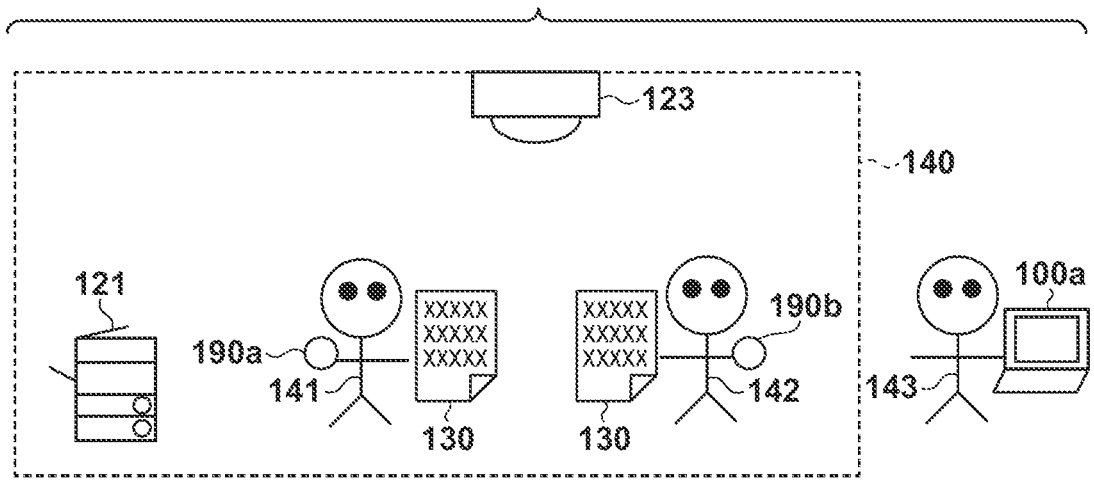
FIG. 3 is a view showing an example of a communication space where the information processing system shown in FIG. 1 is used.

FIG. 3 is a view showing an example of the communication space where the information processing system 110 is used. The communication space is a place where a plurality of participants including persons 141 and 142 communicate. The communication space may be a real space such as a meeting room 140 as shown in FIG. 3. Further, the communication space may be an online virtual space as will be described later.

As shown in FIG. 3, the printing apparatus 121 and the network camera 123 are installed as the peripheral apparatuses 120 in the meeting room 140. The person 141 and the person 142 are gathering in the meeting room 140 as participants of communication such as a meeting. Further, a person 143 exists outside the meeting room 140. Here, the person 143 is not a participant in communication such as a meeting in the meeting room 140 serving as the communication space.

The person 141 wears a mobile terminal 190*a* and has a printed product 130 output from the printing apparatus 121. The person 142 wears a mobile terminal 190*b* and has the printed product 130 similar to the person 141. The person 143 uses an information processing apparatus 100*a*. In the example shown in FIG. 3, a one-to-one meeting between the person 141 and the person 142 will be described as an example, but it may be a meeting in which three or more people participate.

Figure 4:
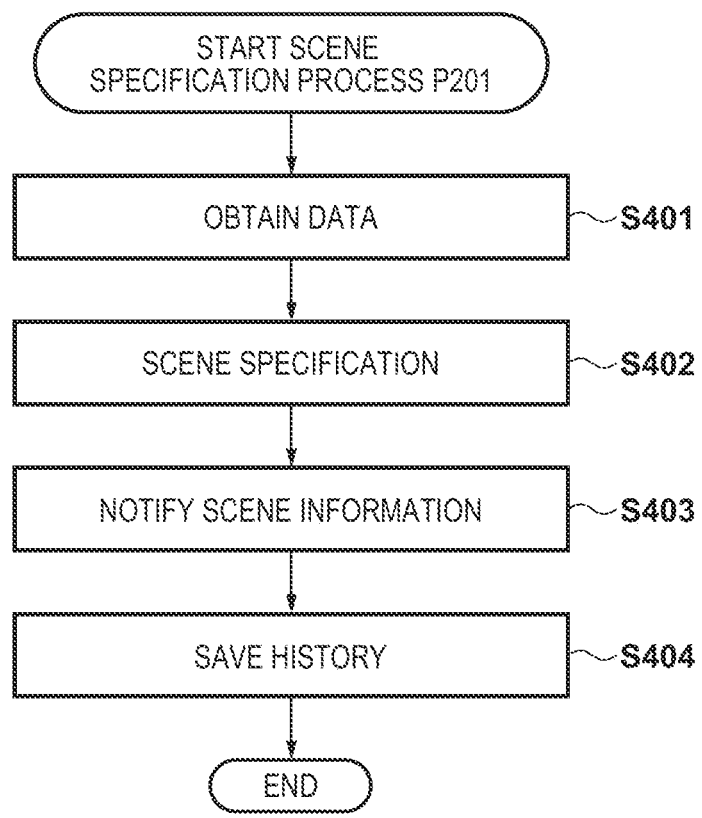
FIG. 4 is a flowchart illustrating an example of a processing procedure of the information processing system shown in FIG. 1.

FIG. 4 is a flowchart illustrating steps of the scene specification process P201. The scene specification process P201 illustrated in FIG. 4 is executed by, for example, the server 160. The scene specification process P201 is implemented by the CPU 102 reading out the program stored in the ROM 103 into the RAM 104 and executing it in the control device 101 of the server 160. Here, the scene specification process P201 is started at regular intervals. However, it may be configured such that the scene specification process P201 is started when the communication between the person 141 and the person 142 is started. More specifically, for example, from the video data captured by the network camera 123, the server 160 (the control device 101 and the CPU 102) may determine that the person 141 and the person 142 enter the meeting room 140, and the scene specification process P201 may be started. Alternatively, for example, an entry/exit management system of the meeting room 140 may be arranged as the peripheral apparatus 120, and the scene specification process P201 may be started when the person 141 and the person 142 enter the meeting room 140.

When the scene specification process P201 is started, in step S401, the CPU 102 of the server 160 requests the peripheral apparatus 120 for data necessary for specifying the scene, and obtains the data from the peripheral apparatus 120. For example, the printing apparatus 121 transmits, to the server 160, the output data including the image information, the document information, and the like of the output product such as the printed product 130. Further, for example, the image capturing apparatus such as the network camera 123 among the peripheral apparatuses 120 transmits, to the server 160, the video data including the captured video information, voice information, and the like. In this case, the image capturing apparatus such as the network camera 123 among the peripheral apparatuses 120 may analyze the video data and transmit, to the server 160, the behavior data specifying the persons 141 and 142 and the behavior of the persons 141 and 142.

Although not shown in FIG. 3, the display apparatus such as the projector 122 or a display among the peripheral apparatuses 120 may be arranged in the meeting room 140. When the display apparatus is arranged, the display data including the image information, the document information, and the like displayed by the display apparatus in the meeting room 140 may be transmitted to the server 160 as the information necessary for specifying the scene.

Then, in step S402, from the various kinds of data obtained from the peripheral apparatuses 120 in step S401, the CPU 102 of the server 160 specifies the scene of the meeting room 140 serving as the communication space. The CPU 102 of the server 160 specifies the scene based on at least one of the above-described image information, text information, voice information, and video information in the communication space.

FIG. 7 shows examples of scene specification results. An output product 702 can be the image information or document information of the output product such as the printed product 130 output from the printing apparatus 121, the image information or document information displayed by the display apparatus such as the projector 122 in the meeting room 140, or the like. A person 703 can be the information of the participants associated with the image information or text information of the output product 702, or the information of the participants in the communication space such as the persons 141 and 142 identified from the voice information or video information obtained by the image capturing apparatus such as the network camera 123. The person 703 may be the information of the participants in the communication space obtained by the entry/exit management system of the meeting room 140. A place 704 is the information of the place of the communication space such as the meeting room 140.

The CPU 102 of the server 160 specifies the scene based on at least one of the above-described image information, text information, voice information, and video information in the communication space. As has been described above, the server 160 obtains any of the image information, the text information, the voice information, and the video information in the communication space (meeting room 140) from the peripheral apparatuses 120 that can communicate with the server 160. Based on the information such as the output product 702, the person 703, and the place 704, the CPU 102 of the server 160 determines the scene of the communication space including a scene specification result 700 and an importance 701. In this manner, in this embodiment, the server 160 (CPU 102) functions as a specification device that specifies the scene of the communication space where the participants communicate.

For example, in a case in which the output product 702 is a result report, the person 141 is a general employee who created the material, the person 142 is a manager who has the approver authority, and a person other than the persons 141 and 142 is also in the room, the scene is determined to be an important report such as a result report. In this case, the importance is determined to be high. The determination criteria are not only limited to predetermined criteria, but also may be appropriately customized by the user registering arbitrary criteria or the like. As has been described above, in step S402, the server 160 specifies the scene including at least one of the information of the discussion in the meeting room 140 serving as the communication space, the information of the participants, and the information of the place of the communication space.

When the scene is specified, in step S403, the CPU 102 of the server 160 may inform the persons 141 and 142 of the scene information (the scene specification result and the importance) via the mobile terminal 190a and the mobile terminal 190b, respectively.

Then, in step S404, the CPU 102 of the server 160 saves the history of the result of the scene specification in the storage device 106, and terminates the scene specification process P201. The history data saved in step S404 is used to visualize, by a graph or the like, the actual result indicating the specific scene and the specific kind of the communication performed in this scene. The user can use this as a reference material when customizing the determination criteria. Further, for example, the CPU 102 of the server 160 may perform machine learning using the history data, generate a learned model that has machine-learned the relationship between the data such as the above-described image information, text information, voice information, and video information in the communication space and the scene information such as the information of the discussion in the communication space, the information of the participants, and the information of the place of the communication space, and save the learned model in the storage device 106. Further, the CPU 102 of the server 160 may specify the scene using the learned model in step S402. This can improve the scene specification accuracy. Further, for example, the CPU 102 of the server 160 may use the learned model to customize the determination criteria of the importance 701 upon specifying the scene. 100471 Next, the emotion analysis process P202 will be described. FIG. 5 is a flowchart illustrating steps of the emotion analysis process P202 in the mobile terminal 190a. The emotion analysis process P202 illustrated in FIG. 5 is implemented by, for example, the CPU 192 reading out the program stored in the ROM 193 into the RAM 194 and executing it in the control device 191 of the mobile terminal 190a. In this embodiment, the emotion analysis process P202 is executed at predetermined intervals. The emotion analysis process P202 can also be executed simultaneously in the mobile terminal 190b.

When the emotion analysis process P202 is started, in step S501, the CPU 192 of the mobile terminal 190a obtains data such as the biological information, image information, and voice information of the person 141 from the sensor 197 as described above. Then, in step S502, the CPU 192 of the mobile terminal 190a determines whether it is required to perform the emotion analysis. Step S502 is inserted to suppress the processing load on the CPU 192 of the mobile terminal 190a, but the emotion analysis step in step S503 may be always performed. For example, if the emotion analysis process P202 has not been executed because it is immediately after activation of the mobile terminal 190a or if a predetermined time has elapsed after the previous execution of the emotion analysis process P202, the CPU 192 of the mobile terminal 190a may determine that it is required to perform the emotion analysis. Further, for example, if the scene information received from the server 160 in step S403 described above has changed or if the data obtained in step S501 has largely changed, the CPU 192 of the mobile terminal 190a may determine that it is required to perform the emotion analysis. If it is determined that it is required to perform the emotion analysis, the emotion analysis process P202 transitions to step S503. If it is determined that it is not required to perform the emotion analysis, the emotion analysis process P202 transitions to step S505. If it is determined that it is not required to perform the emotion analysis, the emotion analysis process P202 may be terminated.

In step S503, based on the data obtained in step S501, the CPU 192 of the mobile terminal 190a quantifies the emotion level of the person 141 such as "calm (normal)", "positive emotion (joy, fun, satisfaction)", "negative emotion (anger, sadness, dissatisfaction)", or "abnormal emotion (impatience, vacant)". The above-described biological information such as the heart rate of the person 141, and the voice information such as the contents, strength, and intonation of the utterance of each of the person 141 himself/herself and the person 142 serving as the communication target can be used for the emotion analysis. Further, the facial expression data of the person 141 and the person 142 based on the video information captured by the network camera 123 may be used for the emotion analysis. In this manner, the CPU 192 of the mobile terminal 190a quantifies the emotion level of the person 141 based on at least one of the biological information, voice information, and video information of the person 141. Further, the emotion level of the person 141 may be quantified based on at least one of the biological information, voice information, and video information of the person 142. In this manner, in this embodiment, the mobile terminal 190a (CPU 192) functions as an analysis device that analyzes the emotion of the person 141 and quantifies the emotion level of the person 141. Similarly, the mobile terminal 1906 can analyze the emotion of the person 142 and quantify the emotion level of the person 142.

When the emotion level of the person 141 is quantified, in step S504, the CPU 192 of the mobile terminal 190a transmits the emotion level to the server 160. In the procedure illustrated in FIG. 5, the emotion level is always transmitted to the server 160 when the emotion analysis is performed in step S503. However, if there is no difference from the previous process result or the difference is small, step S504 may be omitted. Then, in step S505, the CPU 192 of the mobile terminal 190a saves, as a history, the data of the information obtained in step S501 and the emotion level determined in step S503 in the storage device 196, and terminates the emotion analysis process P202.

Next, the notification process P203 will be described. FIG. 6 is a flowchart illustrating steps of the notification process P203 in the server 160. The notification process P203 illustrated in FIG. 6 is executed by, for example, the server 160. The notification process P203 is implemented by the CPU 102 reading out the program stored in the ROM 103 into the RAM 104 and executing it in the control device 101 of the server 160. In the procedure illustrated in FIG. 6, the notification process P203 is started when the emotion level transmitted from the mobile terminal 190a to the server 160 in step S504 is received, but the present invention is not limited to this. For example, the server 160 may start the notification process P203 at predetermined intervals. In this case, when starting the notification process P203, the server 160 may request the mobile terminals 190a and 190b for the data of the emotion level of the persons 141 and 142, respectively.

When the notification process P203 is started, in step S601, the CPU 102 of the server 160 obtains the emotion level transmitted form the mobile terminal 190a in step S504. Further, in step S602, the CPU 102 of the server 160 obtains the latest scene information saved in the storage device 106 of the server 160 in step S404. Steps S601 and S602 may be performed in parallel, or the latest scene information may be constantly obtained.

Then, in step S603, the CPU 102 of the server 160 determines whether to perform step S604 and the subsequent steps in the notification process P203, that is, whether to make a notification (notification determination). For example, if the emotion level obtained in step S601 has changed from the previously obtained emotion level and the emotion level exceeds a set threshold, step S604 and the subsequent steps are performed (YES in step S603). For example, if the emotion level has changed to negative emotion or abnormal emotion, step S604 and the subsequent steps may be performed. Further, if the emotion becomes stronger regardless of the positive, negative, or abnormal emotion, step S604 and the subsequent steps may be performed. That is, the server 160 (CPU 102) functions as at least a part of a notification device that makes a notification if the emotion level exceeds the set threshold. If there is no change in the emotion level, the notification process P203 may be terminated (NO in step S603).

Here, in order to absorb the state difference between the scenes in the communication space, the threshold may be changed based on the information such as the importance 701 and the person 703 of the scene obtained in step S602.

For example, in a case of the scene with the high importance, in order to perform smooth communication in a meeting or the like, it may be set such that the notification is made early. Further, for example, in a case in which the position is largely different between the participants or the like, in order to make a notification before the emotion of the participant in the lower rank largely changes to the negative emotion, it may be set such that the notification is made early. The threshold for each scene may be set by the user or the like in advance. In this manner, the server 160 (CPU 102) can function as a threshold changing device that changes the setting of the threshold for the notification in accordance with the scene.

If the notification process P203 transitions from step S603 to step S604, based on the emotion level obtained in step S601 and the scene information obtained in step S602, the CPU 102 of the server 160 decides the notification target. For example, assume a case in which the emotion level of the person 141 exceeds the set threshold. In this case, the CPU 102 of the server 160 first identifies the person 142 serving as the communication target of the person 141. Based on the scene information obtained in step S602, the CPU 102 of the server 160 may identify, as the communication target, the person 142 who is in the meeting room 140 serving as the communication space together with the person 141. When the person 142 serving as the communication target is identified, the CPU 102 of the server 160 decides the mobile terminal 190b worn by the person 142 as the notification target. In this manner, in this embodiment, the server 160 (CPU 102) functions as an identification device that identifies the person 142 serving as the communication target of the person 141.

In step S605, the CPU 102 of the server 160 makes a notice of execution of the notification to the mobile terminal 190b serving as the notification target decided in step S604. In accordance with the notice of execution of the notification received from the server 160, the mobile terminal 190b notifies the person 142 that the emotion level of the person 141 exceeds the set threshold. For example, the mobile terminal 190b makes the notification using a suitable method such as a vibration function, a loudspeaker for audio output that can be included in the sensor 197 or the like, or screen display on the operation unit 195 or the like. The method of executing the notification in the mobile terminal 190b may be appropriately selected by the CPU 102 of the server 160 in accordance with the arrangement of the mobile terminal 190b. Further, the user such as the person 142 may be able to set a suitable notification method via the operation unit 195 or the like. In this manner, in this embodiment, the server 160 (CPU 102) and the mobile terminal 190b (for example, the vibration function, the loudspeaker of the sensor 197, screen display on the operation unit 195, or the like) cooperate to function as a notification device that notifies the person 142 if the emotion level of the person 141 exceeds the set threshold.

For example, assume a case in which the person 141, who is holding a meeting in the meeting room 140 serving as the communication space, is a subordinate of the person 142. If the person 141 is nervous of the person 142 because they are a superior and is at an anxious emotion level, the communication may not be performed smoothly since the person 141 cannot make a successful presentation or the like. In this case, if the person 141 is notified that the emotion level exceeds the threshold, the person 141 may become more anxious and which would further interfere with communication. Meanwhile, in this embodiment, the person 142 is notified that the emotion level of the person 141 as the subordinate exceeds the threshold. With this, the person 142 can take measures to calm the person 141 who is the subordinate or the like, so that smooth communication is more likely.

Further, for example, assume a case in which the person 141, who is holding a meeting in the meeting room 140 serving as the communication space, is at the emotion level of dissatisfaction with the presentation contents of the person 142. In this case, even if the person 141 is notified that the emotion level of the person 141 exceeds the threshold, smooth communication is unlikely. Meanwhile, in this embodiment, the person 142 is notified that the emotion level of dissatisfaction of the person 141 exceeds the threshold. With this, the person 142 can provide more detailed explanations and supplement the contents, so that smooth communication is more likely.

As has been described above, in this embodiment, the notification that the emotion level of the person 141 exceeds the threshold is made not to the person 141 as the interested party whose emotion level is quantified but to the person 142 serving as the communication target of the interested party. With this, smoother communication is more likely between the plurality of participants having different values and participating in a communication space such as the meeting room 140.

When the notification is executed in step S605, the notification process P203 transitions to step S606, and the effect of the notification in step S605 is determined. More specifically, after the person 142 is notified that the emotion level of the person 141 exceeds the threshold, and a predetermined time has elapsed, the CPU 192 of the mobile terminal 190*a* analyzes the emotion of the person 141 again. For example, the CPU 102 of the server 160 may transmit, to the CPU 192 of the mobile terminal 190*a*, a signal instructing to execute the above-described emotion analysis process P202 again. Further, for example, the CPU 192 of the mobile terminal 190*a* may start the emotion analysis process P202 in accordance with the elapse of a predetermined time from the previous execution of the emotion analysis process P202.

The CPU 102 of the server 160 determines whether the emotion level of the person 141 has improved from the emotion level in step S603. More specifically, similar to the determination in step S603, if the emotion level of the person 141 after the elapse of the predetermined time exceeds the threshold, steps similar to step S604 and the subsequent steps are performed again, and the notification is executed as in step S605. In this case, the notification may be made to the person 142 again. Further, for example, the notification may be made to the person 143 who is not included in the participants in the communication space. That is, if the emotion level of the person 141 does not improve, the CPU 102 of the server 160 may determine that intervention of a third party is required, and make a notice to the information processing apparatus 100*a* of the person 143 registered in advance as a notice destination. For example, the persons 141 and 142 may be subordinates of the person 143.

Step S606 may not necessarily be performed, and the notification process P203 may be terminated after performing step S605. However, when step S606 is performed, step S606 can function as a feedback step for smoother communication in the communication space. For example, step S606 may be performed every time a predetermined time elapses during the meeting in the meeting room 140. For example, step S606 may be repeatedly performed until the person 141 and the person 142 exit from the meeting room 140.

After steps S605 and S606 end, the CPU 102 of the server 160 may save the history data in the storage device 106 in step S607. For example, the saved history data is used to visualize, by a graph or the like, the actual result indicating the specific scene and specific participants of the communication and the specific change in the emotion level of the participant caused by the notification. The user can use this as a reference material when setting the notification threshold for each scene. Further, for example, the CPU 102 of the server 160 performs machine learning using the history data, generates a learned model that has machine-learned the relationship between the notification threshold and the change in the emotion level caused by the notification for each scene, and saves the learned model in the storage device 106. The CPU 102 of the server 160 may use the learned model to automatically change the setting of the threshold for the notification of the emotion level for each scene. With this, it becomes possible to make a notification to the person 142 at a more appropriate timing, so that smoother communication is possible.

In this embodiment, it has been described that the emotion of the person 141 is analyzed and, if the emotion level exceeds the set threshold, a notification is made to the person 142. At this time, the emotion of the person 142 may be simultaneously analyzed (mobile terminal 190*b*) and, if the emotion level of the person 142 exceeds the set threshold, a notification may be made to the person 141. That is, in each mobile terminal 190 included in the information processing system 110, the emotion analysis process P202 of the person wearing the mobile terminal 190 is executed. If the emotion level of the person wearing the mobile terminal 190 exceeds the threshold, a notification that the emotion level exceeds the threshold may be made to the person other than the participant whose emotion level exceeds the threshold, the person serving as the communication target.

The case in which the communication space is a real space such as the meeting room 140 has been described above with reference to FIGS. 2 to 7. However, the information processing system 110 according to this embodiment is not limited to be applied to the case in which the communication space is the real space. The information processing system 110 is also applicable to the communication space in an online virtual space such as an online meeting. Focusing on the differences from the above-described case in which the communication space is the meeting room 140, an online meeting will be described below as an example with reference to FIGS. 8 to 12.

FIG. 8 is a view showing the procedure of processes of the information processing system 110 in this embodiment. The information processing system 110 executes three processes described below. The first process is a scene specification process P801 for specifying the scene of the communication space where participants communicate. The second process is an emotion analysis process P802 for analyzing the emotion of the person using the information processing apparatus 100*a* and quantifying the emotion level of the person in the communication space. The third process is a notification process P803 for identifying a person serving as the communication target of the person whose emotion level is quantified, and making a notification to the person serving as the communication target if the emotion level exceeds a set threshold.

Figure 9:
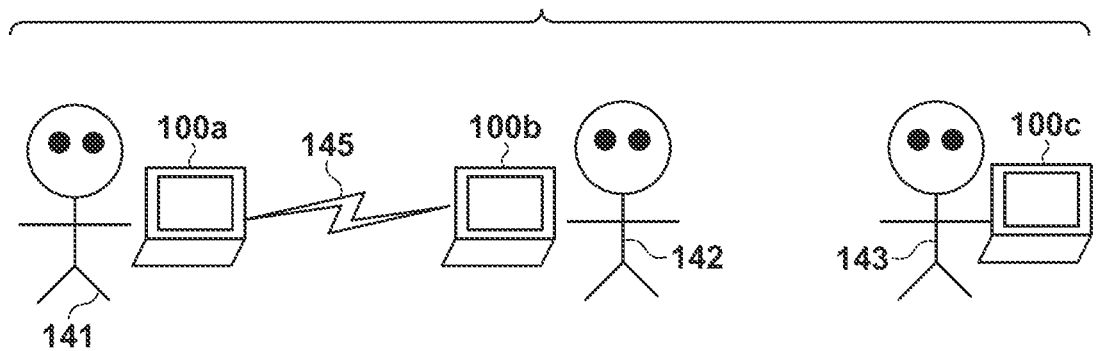
FIG. 9 is a view showing another example of the communication space where the information processing system shown in FIG. 1 is used.

FIG. 9 is a view showing an example of the communication space where the information processing system 110 is used. Unlike the configuration shown in FIG. 3, the information processing apparatus 100*a* used by the person 141 and an information processing apparatus 100*b* used by the person 142 are connected by an online meeting system 145, thereby forming the communication space. Further, an information processing apparatus 100*c* of a person 143, who is not the participant of the communication space, is not connected to the online meeting system 145. In the example shown in FIG. 8, a one-to-one online meeting between the person 141 and the person 142 will be described as an example, but it may be an online meeting in which three or more people participate.

Figure 10:
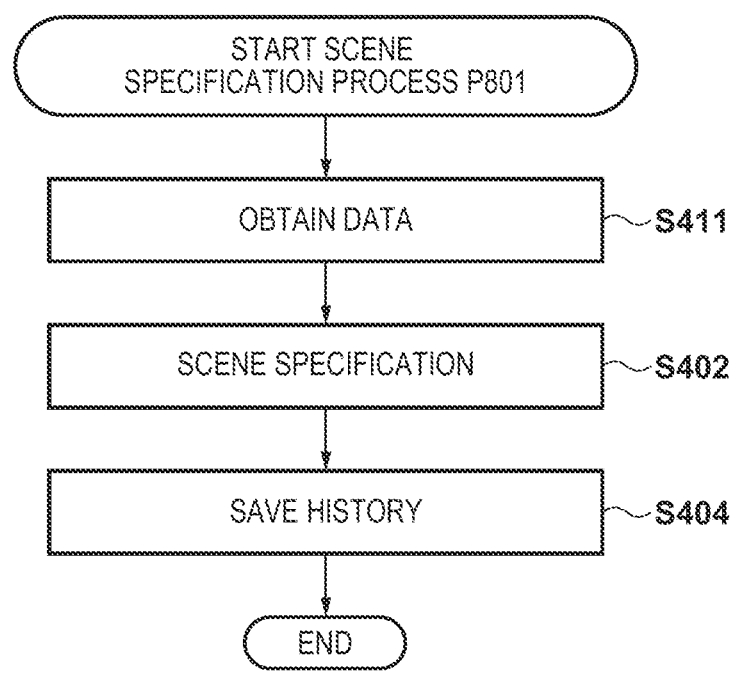
FIG. 10 is a flowchart illustrating an example of a processing procedure of the information processing system shown in FIG. 1.

FIG. 10 is a flowchart illustrating steps of the scene specification process P801. The scene specification process P801 illustrated in FIG. 10 is executed by, for example, the server 160. The scene specification process P801 is implemented by the CPU 102 reading out the program stored in the ROM 103 into the RAM 104 and executing it in the control device 101 of the server 160. Steps S402 and S404 of the scene specification process P801 illustrated in FIG. 10 may be similar to those in FIG. 4 described above. Therefore, the description of steps S402 and S404 will be omitted here, and step S411 will be described.

In this embodiment, the scene specification process P801 is started at regular intervals. However, the scene specification process P801 may be started when the communication between the person 141 and the person 142 is started. For example, the scene specification process P801 may be started when the person 141 and the person 142 connect the information processing apparatus 100a and the information processing apparatus 100b to the online meeting system 145, respectively.

When the scene specification process P801 is started, in step S411, the CPU 102 of the server 160 requests, via the online meeting system 145, the information processing apparatuses 100a and 100b for data necessary for specifying the scene, and obtains the data from the information processing apparatuses 100a and 100b. For example, video data including voice information obtained by a microphone for audio input of the input/output unit 107 of each of the information processing apparatuses 100a and 100b and video information obtained by a camera for image input is transmitted to the server 160. For example, data including text information of chat comments entered via the operation unit 105 of each of the information processing apparatuses 100a and 100b is also transmitted to the server 160. Further, for example, data including image information and text information displayed on the display unit 108 of each of the information processing apparatuses 100a and 100b is transmitted to the server 160. Based on these data, in next step S402, the scene including at least one of the information of the discussion in the online communication space via the online meeting system 145, the information of the participants, or the information of the place of the communication space is specified.

Step S403 is omitted in the scene specification process P801 illustrated in FIG. 10, but step S403 may be performed. In this case, the CPU 102 of the server 160 may notify the persons 141 and 142 of the scene information via the information processing apparatuses 100a and 100b, respectively. For example, the scene information can be displayed on the display unit 108 of each of the information processing apparatuses 100a and 100b.

Figure 11:
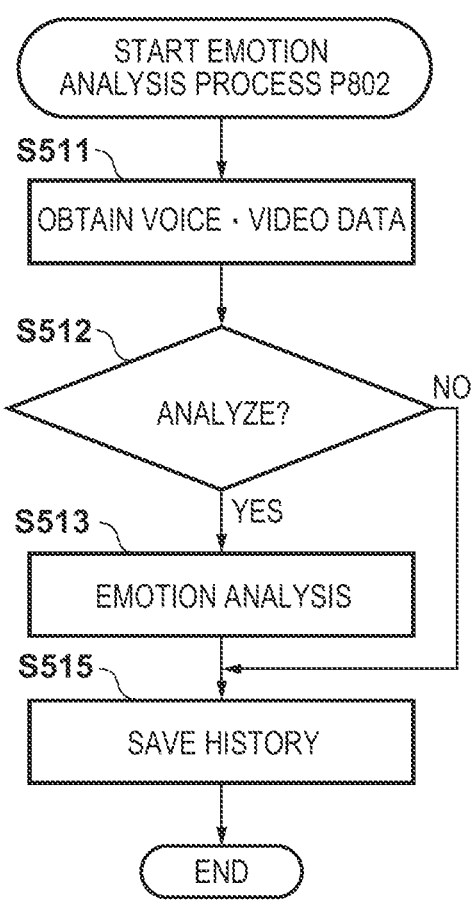
FIG. 11 is a flowchart illustrating an example of a processing procedure of the information processing system shown in FIG. 1.

FIG. 11 is a flowchart illustrating steps of the emotion analysis process P802 in the server 160. The emotion analysis process P802 illustrated in FIG. 11 is implemented by, for example, the CPU 102 reading out the program stored in the ROM 103 into the RAM 104 and executing it in the control device 101 of the server 160. In this embodiment, the server 160 (CPU 102) functions as an analysis device that analyzes the emotion of the person 141 and quantifies the emotion level of the person 141. Here, it is configured that the emotion analysis process P802 is collectively executed on the server 160 connected to the online meeting system 145. However, similar to the case illustrated in FIG. 5 in which the process is executed by each of the mobile terminals 190a and 190b, the process may be executed by each of the information processing apparatuses 100a and 100b. Although the process of quantifying the emotion level of the person 141 will be described as in the above description, the emotion level of the person 142 can be quantified in parallel.

When the emotion analysis process P802 is started, in step S511, the CPU 102 of the server 160 obtains data such as the voice information and video information of the persons 141 and 142 via the online meeting system 145. For example, the video data including the voice information obtained by the microphone for audio input of the input/output unit 107 of each of the information processing apparatuses 100a and 100b and the video information obtained by the camera for image input is transmitted to the server 160.

Here, when the person 141 communicates online such as in an online meeting, the camera of the input/output unit 107, that functions as an image capturing device for capturing the person 141 of the information processing apparatus 100a, operates even when the image of the person 141 is not displayed online. That is, even when the camera image display is turned off on the online meeting system 145, the camera of the input/output unit 107 of the information processing apparatus 100a may operate to obtain images for the emotion analysis process P802.

Then, in step S512, the CPU 102 of the server 160 determines whether it is required to perform the emotion analysis. Since this processing may be similar to step S502 described above except that the determination is performed in the server 160, a detailed description will be omitted.

If it is determined in step S512 that the emotion analysis is required, in step S513, the CPU 102 of the server 160 quantifies the emotion level of the person 141 based on the data obtained in step S511. When the emotion level of the person 141 is quantified in step S512, in step S514, the CPU 102 of the server 160 saves, as a history, the data of the information obtained in step S511 and the emotion level determined in step S513 in the storage device 106, and terminates the emotion analysis process P802.

Figure 12:
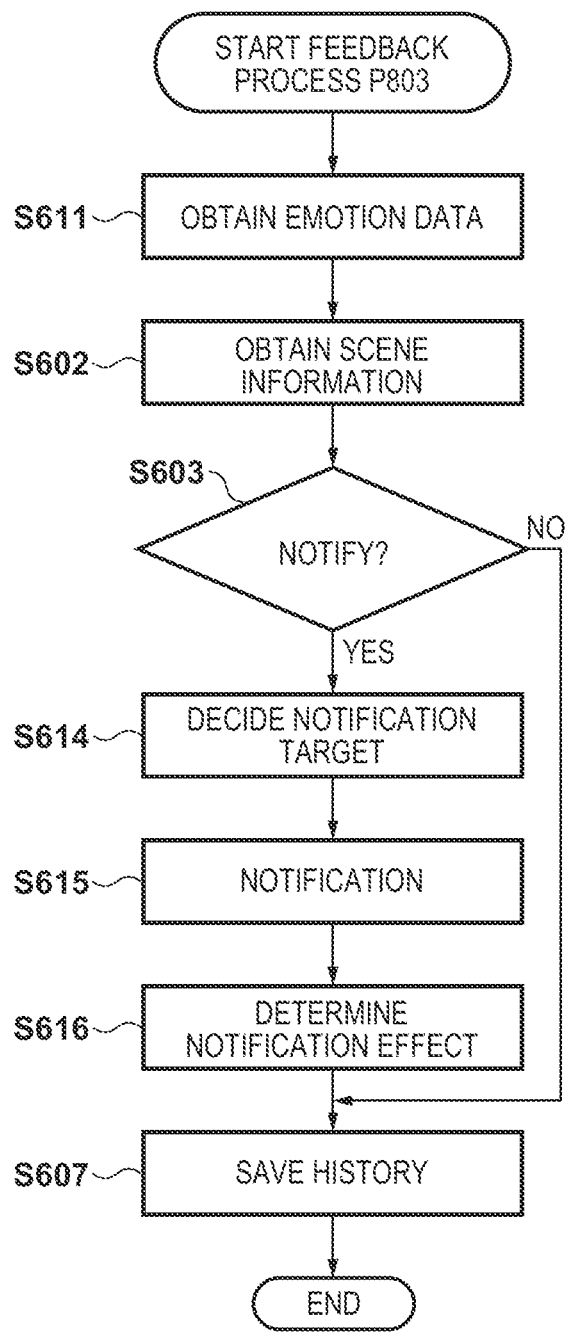
FIG. 12 is a flowchart illustrating an example of a processing procedure of the information processing system shown in FIG. 1.

FIG. 12 is a flowchart illustrating steps of the notification process P803 in the server 160. The notification process P803 illustrated in FIG. 12 is executed by, for example, the server 160. The notification process P803 is implemented by the CPU 102 reading out the program stored in the ROM 103 into the RAM 104 and executing it in the control device 101 of the server 160. Here, the server 160 starts the notification process P803 at predetermined intervals. However, the present invention is not limited to this, and the notification process P803 may be started when the emotion analysis process P802 is terminated.

When the notification process P803 is started, in step S611, the CPU 102 of the server 160 obtains the emotion data saved in the storage device 106 of the server 160 in step S514. Since steps S602 and S603 may be similar to those described using FIG. 6 described above, the description will be omitted here.

If the notification process P803 transitions to step S614, based on the emotion level obtained in step S611 and the scene information obtained in step S602, the CPU 102 of the server 160 decides the notification target. In the configuration shown in FIG. 9, based on the scene information obtained in step S602, the CPU 102 of the server 160 decides, as the notification target, the information processing apparatus 100b connected to the online meeting system 145 serving as the communication space. It can also be said that the CPU 102 of the server 160 identifies the person 142 using the information processing apparatus 100b who serves as the communication target of the person 141 using the information processing apparatus 100a.

Then, in step S615, the CPU 102 of the server 160 makes a notice of execution of the notification to the information processing apparatus 100b serving as the notification target decided in step S614. In accordance with the notice of execution of the notification received from the server 160, the information processing apparatus 100b notifies the person 142 that the emotion level of the person 141 exceeds the set threshold. For example, the information processing apparatus 100b makes the notification using a suitable method such as a loudspeaker for audio output that can be included in the input/output unit 107, or the display unit 108. The method of executing the notification in the information processing apparatus 100b may be appropriately selected by the CPU 102 of the server 160 in accordance with the arrangement of the information processing apparatus 100b. Further, the user such as the person 142 may be able to set a suitable notification method via the operation unit 105 or the like. In this manner, in this embodiment, the server 160 (CPU 102) and the information processing apparatus 100b (for example, the loudspeaker of the input/output unit 107, the display unit 108, or the like) cooperate to function as a notification device that notifies the person 142 if the emotion level of the person 141 exceeds the set threshold.

When the notification is executed in step S615, the notification process P803 transitions to step S616, and the effect of the notification in step S615 is determined. More specifically, after the person 142 is notified that the emotion level of the person 141 exceeds the threshold, and a predetermined time has elapsed, the CPU 102 of the server 160 analyzes the emotion of the person 141 again. The CPU 102 of the server 160 determines whether the emotion level of the person 141 has improved from the emotion level in step S603. More specifically, similar to the determination in step S603, if the emotion level of the person 141 after the elapse of the predetermined time exceeds the threshold, steps similar to step S614 and the subsequent steps are performed again, and the notification is executed as in step S615. In this case, the notification may be made to the person 142 again. Further, for example, the notification may be made to the person 143 who is not included in the participants in the communication space and uses the information processing apparatus 100c not connected to the online meeting system 145. That is, if the emotion level of the person 141 does not improve, the CPU 102 of the server 160 may determine that intervention of a third party is required, and make a notice to the information processing apparatus 100c of the person 143 registered in advance as a notice destination.

Step S616 may not necessarily be performed, and the notification process P803 may be terminated after performing step S615. However, when step S616 is performed, step S616 can function as a feedback step for smoother communication in the communication space. For example, step S616 may be performed every time a predetermined time elapses while the information processing apparatuses 100a and 100b are connected to the online meeting system 145. For example, step S616 may be repeatedly performed until the information processing apparatus 100a and the information processing apparatus 100b are disconnected from the online meeting system 145. After steps S615 and S616 end, a step similar to step S607 described above may be performed.

In this manner, also in an online communication space such as an online meeting, when this embodiment is applied, smoother communication is more likely to be implemented between participants having different values. That is, the information processing system 110 according to this embodiment enables smoother communication in a communication space where a plurality of participants communicate, regardless of whether the communication space is a real space or a virtual space.

Other Embodiments

Embodiment(s) of the present invention can also be realized by a computer of a system or apparatus that reads out and executes computer executable instructions (e.g., one or more programs) recorded on a storage medium (which may also be referred to more fully as 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)TM), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-101026, filed Jun. 17, 2021, which is hereby incorporated by reference herein in its entirety.

What is claimed is:

1. An information processing system comprising:
an analysis device configured to analyze emotion of a first person and quantify an emotion level of the first person;
an identification device configured to identify a second person serving as a communication target of the first person;
a notification device configured to notify the second person if the emotion level exceeds a set threshold;
a specification device configured to specify a scene of a communication space where participants including the first person communicate; and
a threshold changing device configured to change setting of the threshold in accordance with the scene,
wherein, after the notification device notifies the second person that the emotion level exceeds the threshold and a predetermined time has elapsed, the analysis device is configured to analyze the emotion of the first person again, and
wherein, if the emotion level after the elapse of the predetermined time exceeds the threshold, the notification device notifies a third person who is not included in the participants.

2. The system according to claim 1, wherein the analysis device is configured to quantify the emotion level based on at least one of biological information, voice information, or video information of the first person.

3. The system according to claim 1, wherein the scene includes at least one of information of a discussion in the communication space, information of the participants, or information of a place of the communication space.

4. The system according to claim 1, wherein the specification device is configured to specify the scene, in the communication space, based on at least one of image information, text information, voice information, or video information.

5. The system according to claim 4, wherein the specification device is configured to obtain any of the image information, the text information, the voice information, and the video information in the communication space from a peripheral apparatus that can communicate with the specification device.

6. The system according to claim 5, wherein the peripheral apparatus comprises at least one of a printing apparatus, a display apparatus, or an image capturing apparatus.

7. The system according to claim 1, wherein the identification device is configured to identify the second person based on the scene.

8. The system according to claim 1, wherein the second person is included in the participants.

9. The system according to claim 1, wherein the specification device is configured to specify the scene using a learned model that has machine-learned a relationship between at least one of image information, text information, voice information, or video information in the communication space and at least one of information of a discussion in the communication space, information of the participants, or information of a place of the communication space.

10. The system according to claim 1, wherein the threshold changing device is configured to change the setting of the threshold using a learned model that has machine-learned a relationship between the threshold and a change in the emotion level caused by the notification for each scene.

11. The system according to claim 1, wherein, if the emotion level after the elapse of the predetermined time exceeds the threshold, the notification device notifies the second person.

12. The system according to claim 1, wherein the first person communicates online, the analysis device comprises an image capturing device configured to capture the first person, and the image capturing device operates even when an image of the first person is not displayed online.

13. A control method of an information processing system, the control method comprising:
    analyzing emotion of a first person and quantifying an emotion level of the first person;
    identifying a second person serving as a communication target of the first person;
    notifying the second person if the emotion level exceeds a set threshold;
    specifying a scene of a communication space where participants including the first person communicate; and
    changing setting of the threshold in accordance with the scene,
    wherein, after the notifying, the emotion of the first person is analyzed again, and, if the emotion level exceeds the threshold, a third person who is not included in the participants is notified.

14. A non-transitory computer-readable storage medium storing a program for causing a computer to execute a control method of an information processing system, comprising:
    analyzing emotion of a first person and quantifying an emotion level of the first person;
    identifying a second person serving as a communication target of the first person;
    notifying the second person if the emotion level exceeds a set threshold;
    specifying a scene of a communication space where participants including the first person communicate; and
    changing setting of the threshold in accordance with the scene,
    wherein, after the notifying, the emotion of the first person is analyzed again, and, if the emotion level exceeds the threshold, a third person who is not included in the participants is notified.

* * * * *